US006245800B1

(12) United States Patent
Arduini et al.

(10) Patent No.: US 6,245,800 B1
(45) Date of Patent: Jun. 12, 2001

(54) METHOD OF PREVENTING OR TREATING STATIN-INDUCED TOXIC EFFECTS USING L-CARNITINE OR AN ALKANOYL L-CARNITINE

(75) Inventors: Arduino Arduini, Rome; Alessandro Peschechera, Ostia Lido; Paolo Carminati, Milan, all of (IT)

(73) Assignee: Sigma-Tau, Rome (IT)

( * ) Notice: Subject to any disclaimer, the term of this patent is extended or adjusted under 35 U.S.C. 154(b) by 0 days.

(21) Appl. No.: 09/387,522

(22) Filed: Sep. 1, 1999

Related U.S. Application Data

(60) Provisional application No. 60/138,008, filed on Jun. 8, 1999.

(51) Int. Cl.[7] .......................... A61K 31/40; A61K 31/35; A61K 31/21; A61K 31/14
(52) U.S. Cl. .......................... 514/419; 514/460; 514/510; 514/642
(58) Field of Search .................................. 514/460, 546, 514/642, 510, 419

(56) References Cited

FOREIGN PATENT DOCUMENTS

WO96/34846 * 11/1996 (WO) .
WO99/01126 * 1/1999 (WO) .

OTHER PUBLICATIONS

Wanner et al., Hyperlipoproteinemia in chronic renal failure . . . , Cardiology, 1991, vol. 78/3, pp. 202–217.*
Savica et al., A study of the triglyceride–lowering action . . . , Clin. Ter., 1992, vol. 140, pp. 17–22.*

* cited by examiner

Primary Examiner—William R. A. Jarvis
Assistant Examiner—Vickie Kim
(74) Attorney, Agent, or Firm—Nixon & Vanderhye

(57) ABSTRACT

A pharmaceutical composition is described, comprising a lipid-lowering drug such as lovastatin, simvastatin, pravastatin and fluvastatin and L-carnitine or an alkanoyl L-carnitine, which, while conserving the efficacy of the lipid-lowering drug, is substantially devoid of the toxic or side effects typical of such drugs.

10 Claims, No Drawings

METHOD OF PREVENTING OR TREATING STATIN-INDUCED TOXIC EFFECTS USING L-CARNITINE OR AN ALKANOYL L-CARNITINE

This application claim benefit to provisional application No. 60/138,008 Jun. 8, 1999.

The invention described herein relates to a pharmaceutical composition for the treatment of diseases caused by lipid metabolism disorders, and in particular a pharmaceutical composition comprising a statin and L-carnitine or one of its alkanoyl derivatives, useful for the prevention and treatment of statin-induced toxic or side effects.

BACKGROUND OF THE INVENTION

Cardiovascular diseases related to lipid metabolism disorders are very frequent in the industrialised countries. In Italy, for instance, they account for more than 40% of the overall mortality (Capocaccia R., Farchi G., Prati S. et al.: La mortalita' in Italia nell'anno 1989. Rapporto ISTISAN 1992/22). Our knowledge of the relationships between cholesterol and coronary heart disease stems from epidemiological studies conducted in recent years. The conclusions of these studies indicate that the development of severe coronary atherosclerosis is closely related to serum cholesterol levels (McGill H. C. Jr. et al.: The International Atherosclerosis Project. Lab. Invest. 18: 463–653, 1968; Keys A.: Seven Countries: Death and Coronary Heart Disease. Harvard University Press, Cambridge, 1980).

Correction of eating habits through an appropriate diet is always the first measure to be adopted in cases of hyperlipidaemia. Good results, however, are not always achieved owing to widespread intolerance of the strict dietary regimen, to the severity of the hypercholesterolaemia or to genetic-type resistance.

In these cases, to achieve the desired results, that is to say to restore normal blood levels of triglycerides and cholesterol, it proves necessary to resort to pharmacological treatment with lipid-lowering drugs. This category includes both drugs that prevalently reduce cholesterol levels and drugs that prevalently reduce triglyceride levels.

The former group of drugs includes statins, probucol and resins, and the latter group fibrates, nicotinic acid and omega-3-series fatty acids.

The statins (simvastatin, lovastatin, pravastatin, fluvastatin and the like) are hydroxy-methylglutaryl coenzyme A (HMG-CoA) reductase inhibitors. By inhibiting this enzyme, they reduce the hepatic synthesis of cholesterol (Lancet 1994; 334: 1383–1389). To compensate for the reduction in intracellular cholesterol, the liver cell produces more receptors for lipoproteins of the LDL and VLDL series, which in this way are removed from the bloodstream.

In addition, the statins cause less absorption of cholesterol of dietary origin in the intestine and a reduced output of apoprotein B present in low-density lipoproteins (LDL).

The statins are better tolerated than the other cholesterol-lowering agents, but present certain drawbacks: the most common side effects caused by these drugs are gastrointestinal disorders, skin rashes and headache.

A number of patients have complained of sleep disorders (E J Schaffer, N Engl J Med, 319:1222,1988; Lancet, 339:547, Feb. 29, 1992), while significant increases in transaminase activity (GOT and GPT) and in CK compared to basal values have been observed in patients taking statins in doses of 40 mg/kg (Schweiz Med Wochenschr Jun. 29, 1991; 121 (26): 977–83).

Moreover, patients treated with simvastatin present side effects related to myopathy, rhabdomyolysis, muscle pain and increases in serum CK and LDH activity [Dedlypere J. P. & Vermeulen A. (1991) Ann. Intern. Med. 114:342; Bizzarro N. et al. (1992) Clin. Chem. 38: 1504].

EP 0383432 describes the combination of an HMG-CoA reductase inhibitor and coenzyme Q10 for the treatment of skeletal muscle myopathy caused by statins.

It has been reported that statins cause a reduction in the number of deaths due to coronary heart disease, but, on the other hand, an increase in deaths due to other events such as tumours or trauma has been noted in treated patients (Davey-Smith G., Song F., Sheldon T. A., Cholesterol lowering and mortality: the importance of considering initial level at risk. BMJ 1993; 306: 1367–1373; Ravnshov U.; Cholesterol lowering trials in coronary heart disease: frequency of citation and outcome. BMJ 1992; 305: 15–19). Young rats treated with different cholesterol-lowering agents (simvastatin, lovastatin, and pravastatin) show signs of myopathy, when high doses of simvastatin are used (Reijneveld J. C. et al., 1976 Pediatr. Res. 39: 1028–1035). Moreover, Bhuiyan et al. (Bhuiyan J. & Seccombe D. W. 1996 Lipids 31: 867–870) have demonstrated that the administration of lovastatin to rabbits causes a significant reduction in hepatic, cardiac and skeletal muscle L-carnitine.

The results of experiments in animals and in human subjects have suggested that, to reduce cholesterol levels, pharmacological treatment with statins should be used only in patients at high risk of coronary disease in the short term (JAMA, 1996; 275: 55–60).

Equally well known are the triglyceride- and cholesterol-lowering effects of a number of alkanoyl carnitines, in particular of acetyl L-carnitine. U.S. Pat. No. 4,268,524 describes a therapeutic method for increasing the level of high-density lipoproteins (HDL) so as to selectively reduce the LDL+VLDL:HDL ratio in the plasma of patients at risk of cardiovascular disease, in whom this ratio is abnormally high, This method includes the daily administration of 5–50 mg/kg of alkanoyl carnitine or of one of its pharmacologically acceptable salts.

The international patent application WO99/01126 filed in the name of the applicant describes the use of alkanoyl L-carnitine in combination with statins for the treatment of diseases related to lipid metabolism disorders. WO99/01126 does not describe or suggest that L-carnitine or the alkanoyl L-carnitines exert a protective action on statin-induced toxic or side effects.

DESCRIPTION OF THE INVENTION

It has now unexpectedly been found that the co-ordinated use—this term will be defined precisely here below—of L-carnitine or an alkanoyl L-carnitine, in which the linear or branched alkanoyl has 2–6 carbon atoms, or one of their pharmacologically acceptable salts and a statin affords a protective action against statin-induced toxic or side effects.

The well-known lack of toxic and side effects of L-carnitine and of the alkanoyl L-carnitines and the protective action exerted by these compounds on statin-induced toxic or side effects allow the statins to be used at doses higher than those usually administered (10–20 mg/day).

The coordinated use according to the invention is particularly useful and safe for the treatment of both hypercholesterolaemic and/or hyper-triglyceridaemic patients at high risk for cardiovascular disease in the short, medium or long term.

Thanks to the protective effect exerted by L-carnitine or by the alkanoyl L-carnitines, it has been found, in fact, that it is possible to use higher doses of statin than those normally used in human therapy, while the dose of L-carnitine or alkanoyl L-carnitines may be 100–3000 mg/day.

In the context of the invention described herein, what is meant by "co-ordinated use" of the above-mentioned compounds is, indifferently, either (i) co-administration, i.e. the substantially simultaneous administra-tion of L-carnitine or one of the aforesaid alkanoyl L-carnitines or one of their pharmacologically acceptable salts and of a statin, or (ii) the administration of a composition comprising the aforesaid active ingredients in combination and in a mixture, in addition to possible excipients. What is meant by co-administration is also a pack or manufactured article, comprising distinct administration forms of L-carnitine or one of the aforesaid alkanoyl L-carnitines, or one of their pharmacologically acceptable salts and a statin, accompanied by instructions for the co-ordinated simultaneous intake of the active ingredients according to a dosage regimen established by the primary care physician on the basis of the patient's condition.

The invention described herein therefore covers both the co-administration of L-carnitine or one of the aforesaid alkanoyl L-carnitines, or one of their pharmacologically acceptable salts and a statin, and pharmaceutical compositions which can be administered orally or parenterally, comprising a mixture of the two active ingredients.

The subject matter of the invention described herein also includes the use of a therapeutically effective amount of a statin and a detoxifying amount of L-carnitine or an alkanoyl L-carnitine in which the linear or branched alkanoyl has 2–6 carbon atoms, or of one of their pharmacologically acceptable salts for the preparation of a medicinal agent useful for the treatment of diseases caused by lipid metabolism disorders, characterised in that said medicinal agent presents reduced statin-induced toxic or side effects.

A further subject of the invention described herein is the use of a detoxifying amount of L-carnitine or an alkanoyl L-carnitine, in which the linear of branched alkanoyl has 2–6 carbon atoms, or one of their pharmacologically acceptable salts, for the preparation of a medicinal agent useful for the treatment of statin-induced toxic or side effects.

The invention described herein also comprises the use of L-carnitine or an alkanoyl L-carnitine, in which the linear or branched alkanoyl has 2–6 carbon atoms, or of one of their pharmacologically acceptable salts, for the preparation of a medicinal agent useful for the treatment of statin-induced toxic or side effects.

The statin is preferably selected from the group consisting of lovastatin, simvastatin, pravastatin and fluvastatin, while the to alkanoyl L-carnitine is preferably selected from the group consisting of acetyl L-carnitine, propionyl L-carnitine, butyryl L-carnitine, valeryl L-carnitine and isovaleryl L-carnitine or one of their pharmacologically acceptable salts.

More preferably, the statin is simvastatin and the alkanoyl L-carnitine is propionyl L-carnitine or one of its pharmacologically acceptable salts.

Even more preferably, the statin is simvastatin and the carnitine is L-carnitine or one of its pharmacologically acceptable salts.

What is meant by a pharmacologically acceptable salt of an alkanoyl L-carnitine is any salt of this with an acid which does not give rise to toxic or side effects. These acids are well known to pharmacologists and to experts in pharmaceutical technology.

Examples of pharmaceutically acceptable salts of alkanoyl L-carnitines, though not exclusively these, are chloride, bromide, orotate, acid aspartate, acid citrate, acid phosphate, fumarate and acid fumarate, maleate and acid maleate, mucate, acid oxalate, acid sulphate, glucose phosphate, tartrate and acid tartrate.

By favouring the use of larger doses of statins, the combination according to the invention allows better treatment of diseases related to lipid metabolism disorders, thus achieving greater therapeutic success.

The combination according to the invention also contributes to the healing and to prolonging the lives of the patients treated, amongst other things thanks to the increase in therapeutic success rates due to the possibility of maintaining the scheduled treatment protocols for longer periods, without having to discontinue the treatment owing to the toxic or side effects of the statins.

The protective action of L-carnitine or of an alkanoyl L-carnitine on the toxic or side effects of statins has been confirmed by the results of experimental studies, which are reported here below.

Though reference is made in these examples only to L-carnitine, it must, however, be understood that such protection is also afforded by the above-mentioned alkanoyl L-carnitines and by their pharmacologically acceptable salts.

EXAMPLE 1

Male Wister rats aged 23 days and weighing 45–50 g were used. The animals were housed in polycarbonate cages, 5 animals per cage, maintained at a constant temperature of 22±2° C. and at 55±15% relative humidity, with a light-darkness cycle of 12 hours, fed on 4RF21 pellet feed (Mucedola), with tap water to drink ad libitum.

The control group consisted of 14 animals, whereas the groups treated with simvastatin at various doses and with simvastatin plus L-carnitine consisted of 10 animals each, according to the following experimental design:

Control (no treatment);
Simvastatin 70 mg/kg;
Simvastatin 140 mg/kg;
Simvastatin 210 mg/kg;
Simvastatin 70 mg/kg+L-carnitine 400 mg/kg.
Simvastatin 140 mg/kg+L-carnitine 400 mg/kg.
Simvastatin 210 mg/kg+L-carnitine 400 mg/kg.

L-carnitine was given by oral administration via a gastric tube, twice daily (2×200 mg/kg) suspended in 0.5% carboxymethylcellulose (CMC) to the groups treated with statin, or in water when administered alone.

Simvastatin was administered orally suspended in 0.5% carboxy-methylcellulose (CMC) (10 mL/kg).

The duration of the treatment was 9 days.

24 hours after the last treatment, the animals were anaesthetised and blood samples were taken from the sublingual vein.

The blood was centrifuged at 400 rpm for 30 min and the serum thus obtained was used to evaluate plasma levels of CK, GOT, GPT and cholesterol.

The CK, GOT, GPT and cholesterol analyses were carried out using a Cobas Mira S (Roche) automatic analyser and Roche diagnostic kits.

Since the plasma enzyme activity showed a highly skewed distribution, it was decided to analyse the data using the non-parametric Mann-Whitney U test; the test data are shown as median values together with the associated ranges.

The results obtained are reported in Table 1.

TABLE 1

| | | GOT U/L | GPT U/L | CK U/L | Cholesterol mg/dl |
|---|---|---|---|---|---|
| Control | Median | 140.73 | 45.94 | 1056.12 | 73.18 |
| | Range | 96.4–196.4 | 40.3–57.4 | 477.7–1616.4 | 60.3–80.7 |
| Simvastatin 70 mg/kg | Median | 125.68 | 50.65 | 971.51 | 71.35 |
| | Range | 98.8–237.1 | 41.1–73.6 | 396.8–1754.2 | 44.6–87.1 |
| Simvastatin 140 mg/kg | Median | 189.97*** | 69.18*** | 1308.92 | 56.72 |
| | Range | 139.0–293.8 | 40.7–98.7 | 417.8–1836.1 | 44.2–81.3 |
| Simvastatin 210 mg/kg | Mediana | 686.69*** | 93.71** | 1784.32* | 46.54*** |
| | Range | 172.3–5288.8 | 35.5–494.9 | 8808–4887.0 | 35.9–66.1 |
| Simvastatin 70 mg/kg + L-carnitine 200 mg/kg | Mediana | 123.14 | 50.42 | 709.29 | 74.95 |
| | Range | 100.4–204.4 | 37.8–76.6 | 442.0–1840.1 | 56.7–119.4 |
| Simvastatin 140 mg/kg + L-carnitinE 200 mg/kg | Median | 209.45 | 57.49 | 762.53* | 57.21 |
| | Range | 112.3–373.6 | 42.3–138.0 | 350.2–1455.7 | 33.2–75.3 |
| Simvastatin 210 mg/kg + L-carnitine 200 mg/kg | Median | 435.11 | 77.80 | 741.65* | 40.06 |
| | Range | 134.0–2422.7 | 51.8–494.9 | 535.2–2425.0 | 31.3–66.5 |

Mann-Whitney U Test significance: *=$p<0.002$; =$p<0.02$; *=$p<0.05$;

the significance of the groups treated with statin (alone) was calculated versus the control group;

the significance of the groups treated with statin in combination with L-carnitine was calculated versus the group treated with statin alone.

The results presented in Table 1 indicate that the administration of simvastatin at the highest dose (210 mg/kg) caused a substantial and significant increase in plasma GOT ($p<0.002$), GPT ($p<0.002$) and CK ($p<0.05$) compared to controls. At a lower dose (140 mg/kg), simvastatin treatment caused an increase in all the enzyme activities tested, with GOT ($p<0.002$) and GPT ($p<0.02$).

Simvastatin treatment at the lowest dose (70 mg/kg) did not significantly increase the enzyme activity tested.

The cholesterol level was significantly lowered only at the highest simvastatin dose used.

The administration of L-carnitine to the groups treated with is simvastatin showed lower plasma CK activity compared to the group treated with simvastatin alone. Statistically, L-carnitine administration was significantly effective in counterbalancing the plasma CK elevation at the simvastatin doses of 140 and 210 mg/kg (Table 1).

Simvastatin treatment at the lowest dose (70 mg/kg) in combination with L-carnitine reduced plasma CK activity as compared to simvastatin alone at the same dose, though not to a statistically significant extent.

The results of these studies furnish substantial evidence of the protective action of L-carnitine and of the alkanoyl L-carnitines on the toxic and side effects of statins which constitutes the basis for the invention described herein.

In a second experiment conducted in the same way as the first, the only difference being that L-carnitine was administered in the animals' drinking water, comparable results were obtained.

Therefore, a further realisation of the invention described herein comprises the coordinated use of L-carnitine or one of its alkanoyl derivatives or one of their pharmacologically acceptable salts and of a statin according to the above definitions, in the treatment of animals, such as, for example, livestock and, particularly, pets. In this particular realisation, L-carnitine, or one of its derivatives, may be in solid form, such as, for example, fumarate, tartrate or mucate, to be dissolved in drinking water, or in metered-dose liquid form, to be diluted.

What is claimed is:

1. A method of protecting a patient from statin-induced side effects or toxicity arising from the use of a statin, said method comprising the coordinated administration of a detoxifying amount of L-carnitine or of an alkanoyl L-carnitine in which the alkanoyl group is linear or branched and has 2–6 carbon atoms, or one of their pharmacologically acceptable salts, and a statin in an amount greater than a side effect-inducing dose of 20 mg/day.

2. A method of preventing or reducing statin-induced side effects or toxicity arising from the use of a statin in a patent receiving therapy for hypercholesterolemia or hypertriglyceridemia, said method comprising the coordinated administration to the patient a detoxifying amount of L-carnitine or of an alkanoyl L-carnitine in which the alkanoyl group is linear or branched and has 2–6 carbon atoms, or one of their pharmacologically acceptable salts, in an amount of 100 to 3000 mg/day and a statin in an amount greater than a side effect-inducing dose of 20 mg/day.

3. The method according to claim 1 or 2, in which the statin is selected from the group consisting of lovastatin, simvastatin, pravastatin and fluvastatin.

4. The method according to claim 3, in which the statin is simvastatin.

5. The method according to claim 1 or 2, in which the alkanoyl L-carnitine is selected from the group consisting of acetyl L-carnitine, propionyl L-carnitine, butyryl L-carnitine, valeryl L-carnitine, and isovaleryl L-carnitine.

6. The method according to claim 5, in which the alkanoyl L-carnitine is propionyl L-carnitine.

7. The method according to claim 1 or 2, in which L-carnitine is administered.

8. The method according to claim 1 or 2, in which the pharmacologically acceptable salt of L-carnitine or of an alkanoyl L-carnitine is selected from the group consisting of chloride, bromide, orotate, acid aspartate, acid citrate, acid phosphate, fumarate and acid fumarate, maleate and acid maleate, mucate, acid oxalate, acid sulphate, glucose phosphate, tartrate and acid tartrate.

9. The method according to claim 1 or 2, in which the administration is sequential.

10. The method according to claim 1 or 2, in which the administration is substantially simultaneous.

* * * * *